United States Patent [19]

Grossman et al.

[11] Patent Number: 4,986,985
[45] Date of Patent: Jan. 22, 1991

[54] METHOD OF TREATING SKIN VIRUS INFECTIONS

[75] Inventors: Shlomo Grossman; Michael Albeck, both of Ramat Gan, Israel

[73] Assignee: Bar Ilan University, Ramat Gan, Israel

[21] Appl. No.: 116,368

[22] Filed: Nov. 2, 1987

[51] Int. Cl.$^5$ .............................................. A61K 35/78
[52] U.S. Cl. ................................... 424/195.1; 514/934
[58] Field of Search ...................... 424/195.1; 514/934

[56] References Cited

U.S. PATENT DOCUMENTS

| | | |
|---|---|---|
| 2,098,254 | 11/1937 | Mattill et al. . |
| 2,282,808 | 5/1942 | Mushner ..................... 424/195.1 |
| 2,382,242 | 8/1945 | Lindow et al. . |
| 2,890,151 | 6/1959 | White ............................. 514/57 |
| 3,278,383 | 10/1966 | White et al. ................... 514/57 |
| 3,530,217 | 9/1970 | White et al. ................... 514/57 |
| 3,628,971 | 2/1970 | Karchmar . |
| 3,883,505 | 5/1976 | Hamuro . |
| 3,948,801 | 4/1976 | Braddon et al. ............... 252/400 A |
| 4,011,206 | 3/1977 | Higginbotham . |
| 4,075,406 | 2/1978 | Melaga et al. . |
| 4,154,822 | 5/1979 | Polimeni et al. .............. 514/54 |
| 4,162,308 | 4/1979 | Calvin et al. ................. 424/195.1 |
| 4,180,561 | 12/1979 | Vinson ........................... 424/71 |
| 4,321,360 | 3/1982 | Blount ............................ 536/1 |
| 4,352,746 | 10/1982 | Bracco et al. ................. 252/398 |
| 4,361,697 | 11/1982 | Dobberstein et al. ......... 536/128 |
| 4,380,506 | 4/1983 | Kimura et al. ................. 252/398 |
| 4,499,267 | 2/1985 | Seifoni ........................... 44/51 |
| 4,511,559 | 4/1985 | Szendrei et al. ................ 514/54 |
| 4,525,306 | 6/1985 | Yajima .......................... 260/428.1 |
| 4,536,496 | 8/1985 | Shimizu et al. ................. 514/54 |
| 4,670,265 | 6/1987 | Sydiskis et al. ................ 424/195.1 |

FOREIGN PATENT DOCUMENTS

| | | |
|---|---|---|
| 0030444 | 12/1980 | European Pat. Off. . |
| 0054486 | 12/1981 | European Pat. Off. . |
| 0133151 | 7/1984 | European Pat. Off. . |
| 2209856 | 9/1973 | Fed. Rep. of Germany . |
| 3207005 | 9/1982 | Fed. Rep. of Germany . |
| 3130894 | 2/1983 | Fed. Rep. of Germany . |
| 1573315 | 5/1968 | France . |
| 2229388 | 12/1974 | France . |
| 2424024 | 11/1979 | France . |
| 2484836 | 12/1981 | France . |
| 0102809 | 12/1980 | Japan . |
| 0219384 | 5/1983 | Japan . |
| 8101517 | 11/1970 | PCT Int'l Appl. . |
| 8601713 | 3/1986 | PCT Int'l Appl. . |
| 0856914 | 12/1960 | United Kingdom . |
| 1105474 | 3/1965 | United Kingdom . |
| 1141573 | 3/1967 | United Kingdom . |
| 1105769 | 3/1968 | United Kingdom . |
| 1335181 | 10/1969 | United Kingdom . |
| 1337205 | 10/1971 | United Kingdom . |
| 2060378 | 5/1981 | United Kingdom . |
| 2081581 | 7/1981 | United Kingdom . |

OTHER PUBLICATIONS

CTFA Cosmetic Ingredient Dictionary, Third Edition, p. 298.
Nollar Textbook of Organic Chemistry, 2nd, pp. 108–113, and pp. 138–146, (1956).
King J. American Dispensatory, pp. 832–834, and pp. 548–551, (1870).
Patent Abstracts of Japan, Unexamined Appln. C. Field, vol. 4, No. 98 7/80, The Patent Office Japanese Gov't. p. 134 C. 18–Kokai-No. 55-62 005, (Kurorera).
Patent Abstracts of Japan C Section vol. 1, No. 27 3/77, p. C 969 Kokai-No. 51-142, 514 (A. Fukuda).
Patent Abstracts of Japan. C Section, vol. 7:48 5/77, p. 6 77. Kokai-No. 52-3, (Jafcee Foods).
Journal of Food Science, vol. 36, (1971), p. 57. A. Pinsky et al., "Lipoxygenase Content and Antioxidant Activity of some Fruits and Vegetables."

Primary Examiner—John W. Rollins
Attorney, Agent, or Firm—Ladas & Parry

[57] ABSTRACT

Water-soluble plant extracts, and fractions separated from such extracts by chromatography, which provide an antioxidant effect when applied to the skin, are utilized in a method of treating virus skin infections and resultant skin conditions, e.g. warts. Preferred plants are Trifolium, Medicago, Nicotiana, Zea, Pennisetum, Algae and Allium, and members of the order Chenopodiales such as the families Chenopodiaceae and Aizoaceae.

38 Claims, 11 Drawing Sheets

METHOD OF TREATING SKIN VIRUS INFECTIONS

FIELD OF THE INVENTION

This invention relates to a method for the treatment of skin virus infections and of skin conditions resulting from such infections.

BACKGROUND OF THE INVENTION

The present applicants have previously discovered that antioxidants which are stable under ambient conditions for extended periods may be obtained by water extraction of plant tissues, and that such antioxidants are absorbed percutaneously, and exert an antioxidant effect on the outer and inner layers of the skin. These effects are advantageously obtained when the antioxidant is applied to the skin as a dispersion in a hydrophilic or hydrophobic base. The observable results of the application of the antioxidant comprise a softening of the skin which is detectable by touching with the fingertips, as well as a reduction in the peroxide level of the skin.

A vast literature exists relating to the treatment of diseases of various kinds, with substances obtained from plants.

Thus, for example, in GB No. 1105769 (Seifert), fully grown plants of the Urticaceae species (e.g. nettles) are fertilized with urine of persons having certain diseases (diabetes, cancer or blood diseases) and are made up into aqueous solutions or tinctures. The resultant homeopathic preparations may be used to treat these diseases, by the internal administration route.

In GB No. 1141573 (Eiji Yamada), there are disclosed substances said to stimulate the function of the reticuloendothelial system, which are obtained by treating unicellular green algae successively with water, alkali and (optionally) acid, removing impurities from each extract by precipitation using lead acetate, and precipitating the desired materials from the respective filtrates by adding alcohol.

In GB No. 1335181 (Cobb), species of plants defined as belonging to the family Compositae tribe Cynareae, subtribe Centaureineae are subjected to fractionation of the juice and/or solvent extraction (e.g. with ethanol or chloroform) of the plant, to give a substance having antineoplastic activity. The plant material may for example be crushed by pressure to extract the juice, and the latter is tested for activity either undiluted or diluted.

In GB No. 1337205 (Yoshizo Sakamoto et al), specified materials of plant origin are subjected to dry vacuum distillation at 40° to 60° C. Both residue and distillate are pharmacologically active.

In EP No. 0030444 (Yasuhiko Kojima et al), a substance having interferon inducing activity is extracted (e.g. with water) from the tissues of plants belonging to specified botanical genuses.

In WO 81/01517 (Kazuyoshi Morita), an active fraction containing mutagenicity-inhibiting material, which is water soluble, is isolated and purified from burdock juice.

None of the foregoing patents relates to the treatment of skin viral diseases by topical administration of an active substance.

In GB No. 1105474 (Sela et al), virus infected plant tissue is macerated with water and infective virus removed from the filtrate; the latter contains a substance of antiviral activity which may be further concentrated by chromatography. The product is stated to apparently contain protein and RNA. Experiments show that it prevents or reduces the level of viral infections in plants. No supportive data is provided to support a suggestion that it may also be used for prevention or treatment of virus infections in livestock and humans. There is no evidence that the material has antioxidant properties or that it can be used to treat viral skin infections in animals or humans by topical application. The data given appears to show merely that an antiviral factor extracted from a plant infected with a particular virus is specific for treatment of the same virus.

In EP No. 0133151 (Berman), there is disclosed an ointment for the treatment of what are termed "skin diseases" (but which on closer inspection appear to be rather intrinsic conditions such as psoriasis, hemerrhoids, varicose veins, acne and eczemas) which comprises an emulsion comprising extracts of a plurality of plants, selenium rich water and a carrier. There is no disclosure of any aqueous extract of plants having antioxidant activity; only extracts in alcohols are mentioned specifically.

In EP No. 0054486 (Cervelle et al), a pharmaceutical composition which may be used for topical treatment of skin virus diseases contains as active ingredient the total extract of Hedysarum Fructescens Willd, consisting essentially of flavanoids, catecholic tannins and phenolic acids, in absence of alkaloids. In practice, the extraction agent is alcohol, aqueous alcohol or propyleneglycol. Although this patent relates to an active ingredient for the topical treatment of skin virus, there is no evidence that the invention thereof can be effected by utilization of extraction with water. It is also self-evident that extraction with water according to the present invention would leave behind water-insoluble materials extracted by the organic solvents, used for the purpose of total extraction, according to Cervelle. Further, this patent contains no disclosure that the extracted ingredients provide an antioxidant effect when applied to the skin, as is required by the present invention.

It has now been surprisingly discovered by the present inventors, and this discovery forms the basis for the present invention, that antioxidant materials extracted from plant tissue with water, and which provide an antioxidant effect when applied to the skin, are useful in treating viral infections of the skin, and conditions of the skin resulting from such viral infections. So far as the applicants are aware, there is no established relationship between antiviral activity and antioxidant activity, such has been unexpectedly found in the present instance. Moreover, the antioxidant materials described herein have been found to be useful for inhibiting at least certain kinds of warts which are known to be due to viruses.

The stable, water soluble plant-extracted antioxidants which have found to be useful in the present invention, are disclosed in U.S. patent application Ser. No. 846,599, filed Mar. 31, 1986, (a continuation-in-part from application Ser. No. 726,540, filed Apr. 24, 1985) as well as in European Patent Application No. 0201956 published Nov. 20, 1986.

SUMMARY OF THE INVENTION

The invention accordingly relates to a material which provides an antioxidant effect when applied to the skin, for use in a method of treatment of virus skin infections and of skin conditions resulting from such infections, said material being characterized by stability for an extended period of time under ambient temperature and pressure, at least in the dry state, and being selected from water soluble extracts prepared from plant tissue and fractions separable from said extracts by chromatography. The antioxidant material may be prepared as described herein.

The invention also relates to a composition of matter for use in a method of treatment of virus skin infections and of skin conditions resulting from such infections, which comprises a stable antioxidant material as defined above, or which has been prepared by a process as described herein, together with an inert diluent or carrier which is adapted for application to the skin.

Such a composition of matter may be for example in the form of a gel, ointment, salve, hydrophilic cream, hydrophilic lotion, hydrophobic cream or hydrophobic lotion, or an aqueous solution, and may comprise as a further ingredient a local anaesthetic.

The invention additionally relates to use of a material for the manufacture of a medicament for therapeutic application in the treatment of skin virus diseases and of skin conditions resulting therefrom, the said material being as defined above.

The plant tissues from which the water soluble antioxidants may be obtained are for example the leaves of Trifolium (clover), Medicago (*Medicago sativa*: alfalfa), Zea (*Zea mays*: corn), Nicotiana (*Nicotiana tabacum*: tobacco), Pennisetum, Allium (onion and garlic), Algae and tissues of plants of the order Chenopodiales. The order Chenopodiales comprises the plant families Aizoaceae, Amaranthaceae, Caryophyllaceae, Chenopodiaceae, Nyctaginaceae, Phytolaccaeae and Portulacaceae; presently preferred families are Aizoaceae and Chenopodiaceae. Other suitable plants may also be utilized.

Examples of the family Chenopodiaceae are Spinacia (e.g. *Spinacia oleracea*: spinach), Atriplex, e.g. "Mountain Spinach" (*Atriplex hortensis*), otherwise known as "Orach", and Beta, e.g. the beet varieties included within *Beta vulgaris*. An example of the family Aizoaceae is Tetragonia, e.g. "New Zealand Spinach" (*Tetragonia expansa*).

The present invention thus makes available a method of treating virus skin infections and skin conditions resulting from such infections, which comprises applying to the skin having such infections or conditions, a material which is characterized by stability for an extended period of time under ambient temperature and pressure, at least in the dry state, and by the fact that it provides an antioxidant effect when applied to the skin, and which is selected from water soluble extracts prepared from plant tissue and fractions separable from said extracts by chromatography.

DETAILED DESCRIPTION OF THE INVENTION

Figure 1:
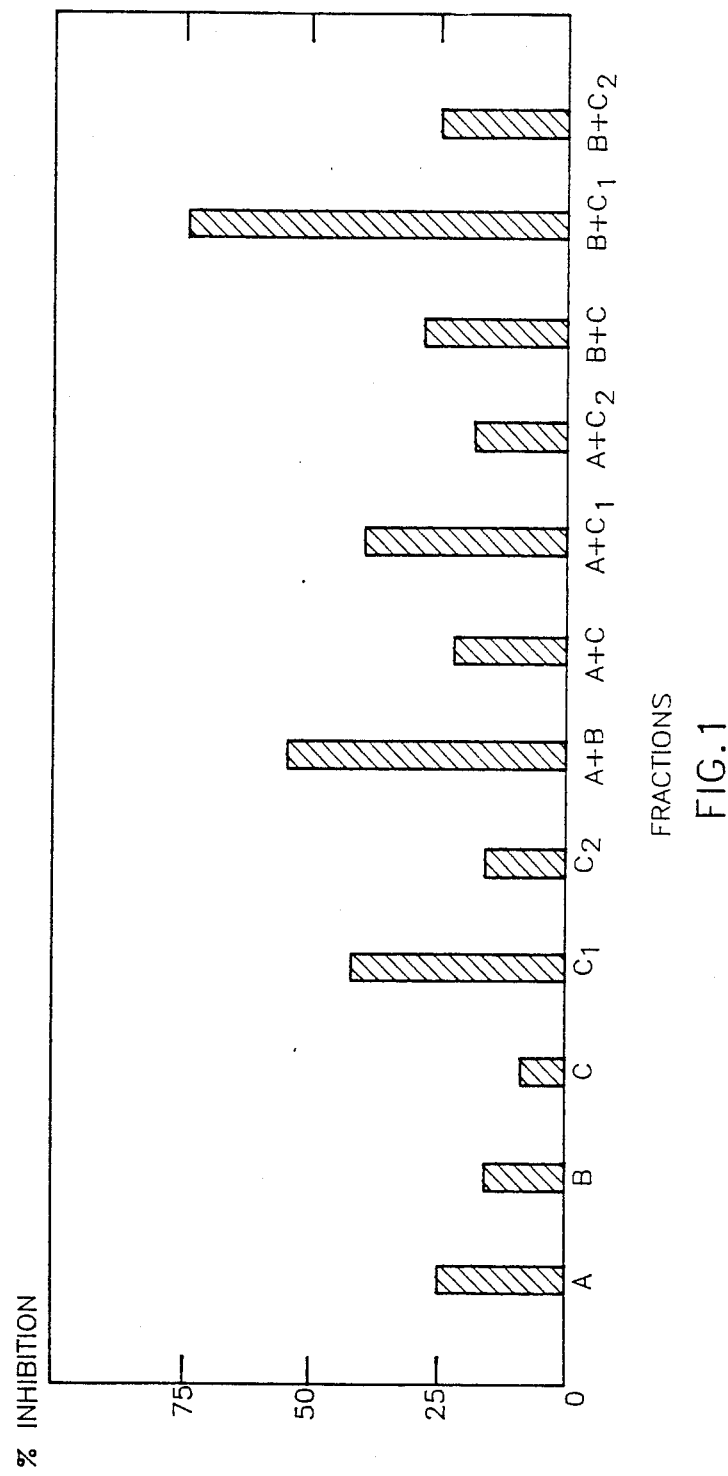
FIG. 1 is a chart which shows the antioxidatively synergistic results of the use of selected antioxidant fractions.

The present invention provides antioxidant materials and compositions containing them for the antiviral use described and claimed herein. These materials are of course capable of being absorbed into the skin, and they have been found to lower the peroxide level of the skin. The plants which may be utilized as a source of the water soluble extract include the plant tissues of selected species such as the stems and green leaves selected from the group consisting of Trifolium, Medicago, Zea, Nicotiana, Pennisetum, Algae, Allium and members of the order Chenopodiales, e.g. of the families Chenopodiaceae (e.g. Spinacia, Atriplex and Beta) and Aizoaceae (e.g. Tetragonia). Other plants may be utilized if an aqueous extract of the green leaves provides an antioxidant effect when it is applied to the skin. The antioxidant effect may be determined by the thiobarbituric acid (TBA) test. This test is described in Food Res. 23: 620 (1958). Generally the level of peroxide in the skin may be determined by assay of a sample of untreated skin which is peeled from a test animal. A preweighed sample from 10 to 50 mg. is homogenized in 0.2M phosphate buffer pH 6.5 and centrifuged. The supernatant is collected and the peroxide level is determined using the TBA test. A sample of skin from the same animal which has been treated with the antioxidant according to the invention is also peeled and the peroxide level is determined. A reduction in the peroxide level of about 35%, when an antioxidant according to the invention is applied as 0.5% w/w dispersion in a petrolatum base, may serve as the criterion for determining if a given plant extract is a useful antioxidant.

As will be apparent to those skilled in the art, the antioxidant properties of the material utilized according to the present invention may be determined in a manner other than the TBA test described above. By way of example only, it has been found that the aqueous extracted plant-derived materials are useful in the present invention, and provide an antioxidant effect when applied to the skin, if they inhibit the lipoxygenase-catalyzed oxidation of linoleic acid.

The inert diluent or carrier which is adapted for application to the skin may be any liquid or semisolid type of material that is compatible with the plant extract and non-irritating to the skin.

The water-soluble antioxidant may be extracted from the plant material using a plant to water ratio in the range of 0.5:100 to 1.0:0.5 (w/v), preferably 2:1 (w/v), after comminution of the plant material. The comminution may be carried out at temperatures within the range of about 4° to about 100° C., e.g. at about 25° C., using a blender, grinding apparatus or any other type of apparatus which will cause fragmentation of the cell walls. The extracted plant material is separated using filtration, centrifugation, decantation, froth flotation, or any other conventional method used for separating a solid from a liquid. Since it has been found that the antioxidant materials are in general sufficiently stable, not to be adversely affected by boiling with water, in an alternative embodiment the plant material may be extracted by boiling with water, and comminution is not essential.

The crude antioxidant may be used as obtained from the plant, either in dilute form or as an aqueous mixture or as a purified extract. Generally it is preferred to separate the aqueous extracting medium from the dissolved antioxidant by evaporation or lyophilization of the liquid portion to provide a dry, water soluble antioxidant. The crude extract may be purified using chromatographic techniques.

Generally, the powder is dissolved in water to form a 10 to 30% w/w solution which is applied to the top of the column and is allowed to move through the column. The various fractions are eluted using water as washing medium and the various fractions are separately collected. The individual fractions may be further purified by a second chromatographic procedure using a packing medium having a smaller pore size than in the preceding step.

Sephadex G-25 may be utilized as a chromatographic column separation medium to resolve the crude extract from spinach into a brown fraction, a yellow fraction and an orange fraction. The orange fraction may be extracted with water and further separated chromatographically using a Sephadex G-10 column. Sephadex G-25, medium grade, is dextran that has been cross-linked with epichlorohydrin and has a pore size of 50-150 $\mu$m. Sephadex G-10 is dextran that has been cross-linked with epichlorohydrin and has a pore size of 40-120 $\mu$m. Thin layer chromatography is utilized to separate a yellow fraction from the orange fraction. The Sephadex materials are described in Gel Filtration Theory and Practice, Pharmacia pp. 1-64, which is incorporated by reference. The applicants have isolated several different active antioxidant fractions, which may be used separately or in combination. Several of the combined fractions have been shown to have higher antioxidant activity than the crude fraction. The relative amounts of the brown, orange and yellow fractions may be varied to give optimum antioxidant activity. Generally, any two fractions may be used for the antiviral use of the present invention at weight ratios of 1:99 to 99:1, based on the total weight of the combined fractions. However, it is also within the scope of the invention to combine together more than two fractions.

The total amount of antioxidant that may be used in the antiviral compositions may vary from about 0.005 to about 5%, preferably from about 0.1 to about 1%, by weight, of the total weight of the product. As has been stated, these compositions may be for example in the form of a gel, ointment, salve, hydrophilic cream, hydrophilic lotion, hydrophobic cream or hydrophobic lotion, or an aqueous solution, and may include for the relief of discomfort a further ingredient, in particular a local anaesthetic such as 1% benzocaine and the like. The antiviral compositions of the invention are applied topically in a manner to be determined by the physician who will take into consideration such factors as the nature and severity of the infection or of the condition resulting therefrom. Purely by way of example, the isolated crude material which has not been subjected to chromatographic separation may be made up into an approximately 1% aqueous solution and applied to the effective parts for a period ranging from e.g. 3 days to 2 or 3 weeks, the number of applications per day being e.g. 1-3. To ensure the non-reappearance of the condition, it is generally desirable to continue treatment for several days after the symptoms have disappeared. This treatment has been found to be especially efficaceous in the treatment of warts due to viruses.

It may be noted that apart from its antiviral effect, the antioxidant has incidentally a protective effect against damage to the skin that is induced by ultraviolet light having a frequency in the range of 200-340 nm. Therefore, the antioxidant which is applied to the skin for its antiviral effect, also prevents damage caused by radiation from natural sources such as the sun, or from artificial sources; accordingly, to obtain a desirable combinative effect, it is also possible to add to the compositions as a further ingredient, a sunscreen agent such as PABA.

Both crude and purified antioxidants in accordance with the invention are stable to high temperature, e.g. at the temperature of boiling water for 30 minutes. Moreover, they have good stability for extended periods under ambient conditions. By way of example, the crude extract from spinach in powder form has been kept for more than one year at room temperature, without any loss in its antioxidant activity.

Toxicity studies have been carried out using both crude and purified fractions, and no pathological changes have been detected when the materials have been administered by injection or orally.

Besides their skin antiviral activity, and the prevention of damage to the skin caused by natural radiation, the antioxidant materials have also been shown to be effective in inhibiting skin cancer such as squama cell carcinoma which is induced by dimethylbenzoicanthrene and 4B-phorbol 12-myristate-13-acetate, and ultraviolet light.

"New Zealand Spinach" (*Tetragonia expansa*) may be substituted for the spinach (*Spinacia oleracea*) in the detailed description herein, including the description of the preferred embodiments which follows, with comparable results.

DESCRIPTION OF THE PREFERRED EMBODIMENTS

Leaves from *Spinacia oleracea* were homogenized with $H_2O$ at 25° C. at a ratio of 2:1 (w/v) in a Waring blender for 5 minutes. The resulting homogenate was filtered through cheesecloth and then centrifuged at 15000× g for 10 minutes. The supernatant was collected and lyophilized.

The isolation and purification of antioxidant fractions from the crude homogenate preparation was achieved through gel filtration followed by preparative TLC or HPLC. 1 g. of the lyophilized powder of the crude homogenate was dissolved in 5 ml. $H_2O$ and after centrifugation at 20000× g for 10 minutes, the supernatant was applied to a Sephadex G-25 column (40 cm. ×2.5 cm.), equilibrated and eluted with water. Fractions of 5 ml. were collected and each was assayed for antioxidant activity. The antioxidatively active fractions (A, B and C) were pooled (fraction A has a brown, B a yellow and C an orange color), and lyophilized. Fraction C was further purified. The lyophilized material of fraction C was dissolved in water to form a 20% solution (w/v), centrifuged at 20000× g for 10 minutes, and the supernatant was chromatographed on a Sephadex G-10 column (40 cm.×2.5 cm.), and equilibrated with water. Fractions were collected, pooled and lyophilized as before. Lyophilized fraction C("$C_1$") was dissolved in a minimum amount of water, applied to 0.2 mm. silica gel plates (DC-Karten SIF, Riedel-Dollaen AG., sleeze-Hanover) and developed in 30:60 v/v $H_2O$-ethanol. The active fraction was identified by its weak (pale) yellow color and was extracted from the silica gel plate with water and lyophilized.

Figure 7:
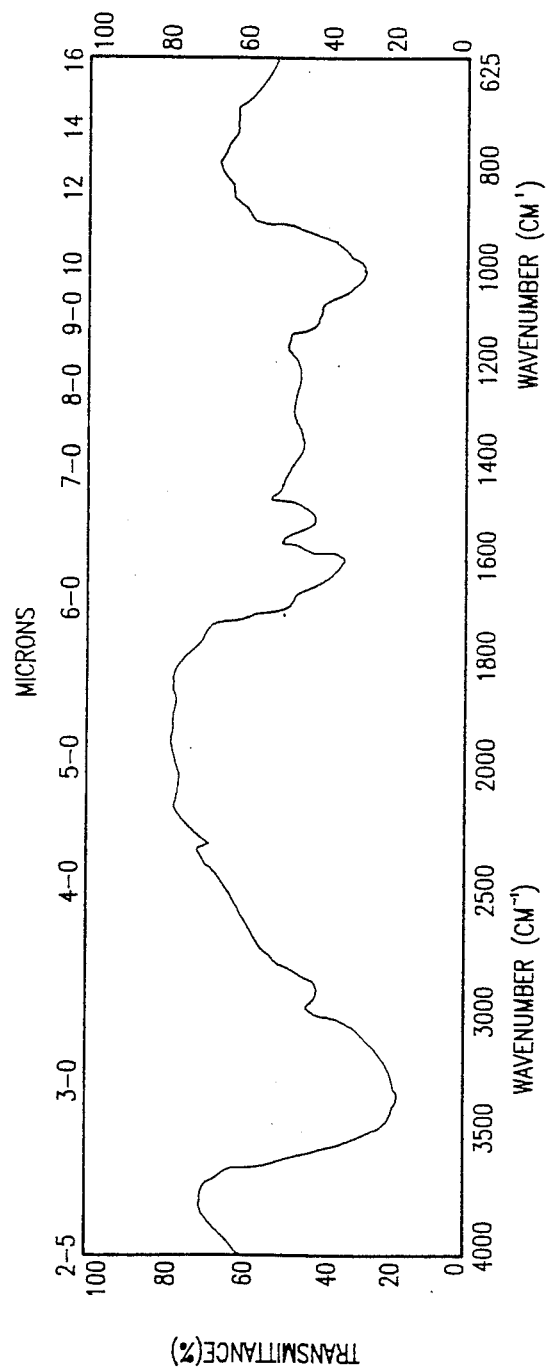
FIG. 7 shows an infrared curve of the antioxidant fraction $A_1$ of the invention, isolated from spinach.

A further purification was carried out using DEAE cellulose (small size). The fraction identified hereinabove as A was dissolved in water and passed through a 5 cm.×1 cm. column packed with DEAE cellulose (small size). (Alternatively, the column packing may be Ecteola, a condensation product of cellulose with epichlorohydrin and triethanolamine having a capacity of 0.3 to 0.4 meq./g. and a particle size 0.05-0.2 mm.) The column was equilibrated with water that was acidified to a pH of 5-6 with 0.2N HCl. The column was eluted with a solution of HCL, pH 2.0 and the eluted material was recovered as a powder by vacuum evaporation. A pure product ($A_1$) was obtained which had the infrared curve of FIG. 7. The powder was further purified by dissolving in water at a concentration of 20 $\mu$g./ml. and passing through a high pressure liquid chromatography silica 60 column (250 mm.×4 mm.), with a 90:10 solution of water:acetonitrile applied at a rate of 0.5 ml./min. A fraction was obtained which had a retention fraction at 5.4 nanometers (UV absorption).

EXAMPLE 1

Separation and Characterization of Antioxidant Fractions

From the crude extract of the plant material, 3 antioxidatively active fractions (A, B and C) were obtained following the first step of purification. Fraction C was further purified on a column packed with Sephadex G-10 and two other active fractions were obtained by elution with water ($C_1$—dark brown and $C_2$—yellow orange). Fraction $C_1$ was finally purified using HPLC. In studying the antioxidant activity of the crude plant extracts and the isolated fractions, both the inhibition of linoleate oxidation by lipoxygenase and the inhibition of autooxidation of peroxides were used as criteria for antioxidant activity.

The antioxidant fractions exhibited antioxidatively synergistic activity. The synergism obtained with the natural isolated antioxidants is shown in FIG. 1, which depicts the percentage inhibition on lipid oxidation of 1 mg. each of single purified antioxidant fractions, as well as the analogous percentage inhibition using combinations of 0.5 mg. each of two such fractions. By way of example, it may be seen that this synergism increased the potency produced by the compounds from 167% (B+$C_2$) up to 250% (A+B), without increasing the total antioxidant content.

Since lipid peroxidation catalyzed by hemeproteins is a basic deteriorative and pathological reaction, the effectiveness of the isolated fractions to prevent such peroxidation was followed. It was found that the isolated fractions prevent such peroxidation induced by haemoglobin, cytochrome C and myoglobin, in a similar way to the inhibition of lipoxygenase-induced oxidation.

The purified antioxidant fractions retained their antioxidative activities for months, without any loss, when kept at room temperature. Moreover, boiling the purified antioxidants for up to 30 minutes, did not reduce their antioxidant capacity.

Figure 3:
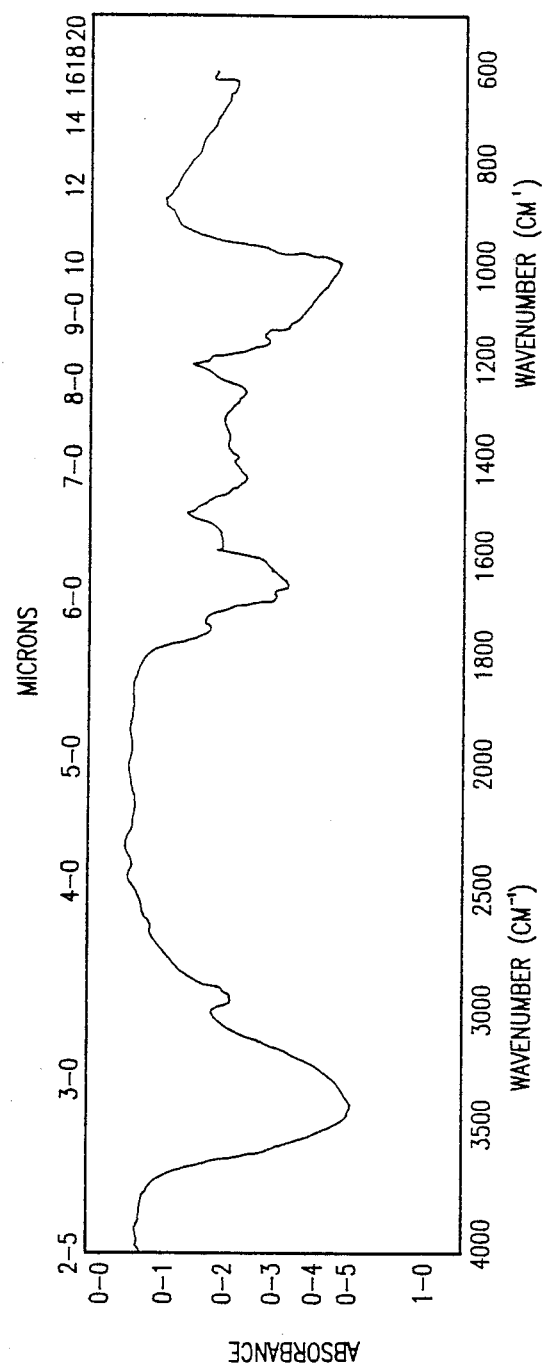
FIG. 3 shows an infrared curve of the antioxidant fraction A of the invention, isolated from spinach.

The following infrared data was obtained from the spinach-derived fractions:

A: (see FIG. 3) broad band at 3400 cm.$^{-1}$, strong bands at 1050 and 1650 cm.$^{-1}$, weak bands at 1250 and 1430 cm.$^{-1}$.

Figure 4:
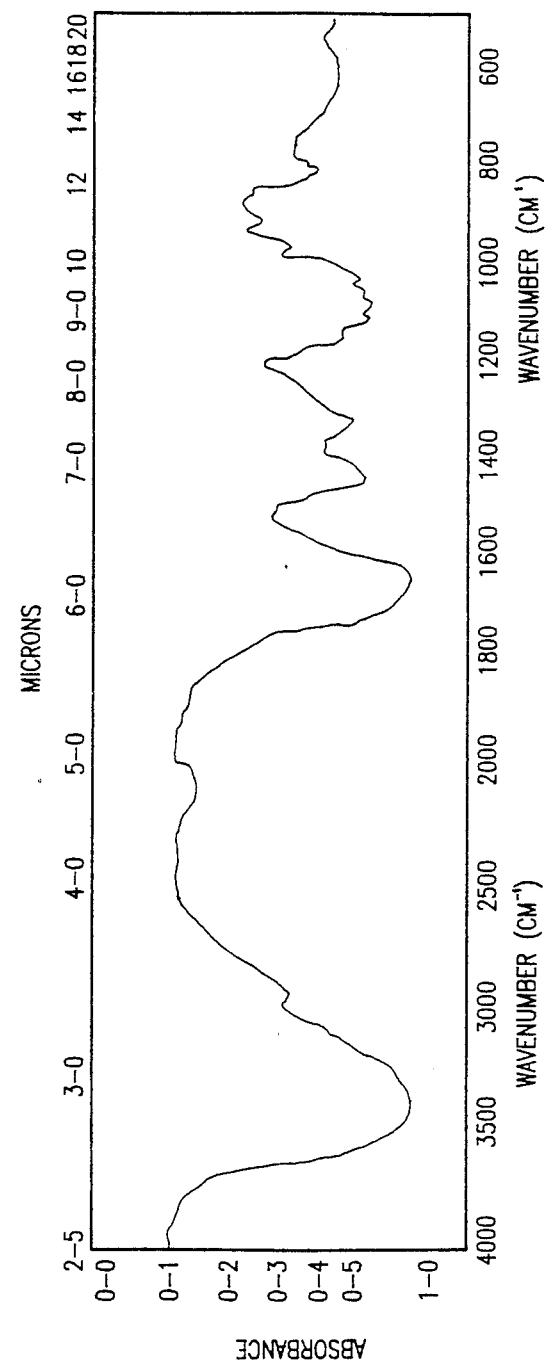
FIG. 4 shows an infrared curve of the antioxidant fraction B of the invention, isolated from spinach.

B: (see FIG. 4) broad bands at 3400, 1640 and 1080 cm.$^{-1}$, additional bands at 1420, 1300 and 810 cm.$^{-1}$.

Figure 5:
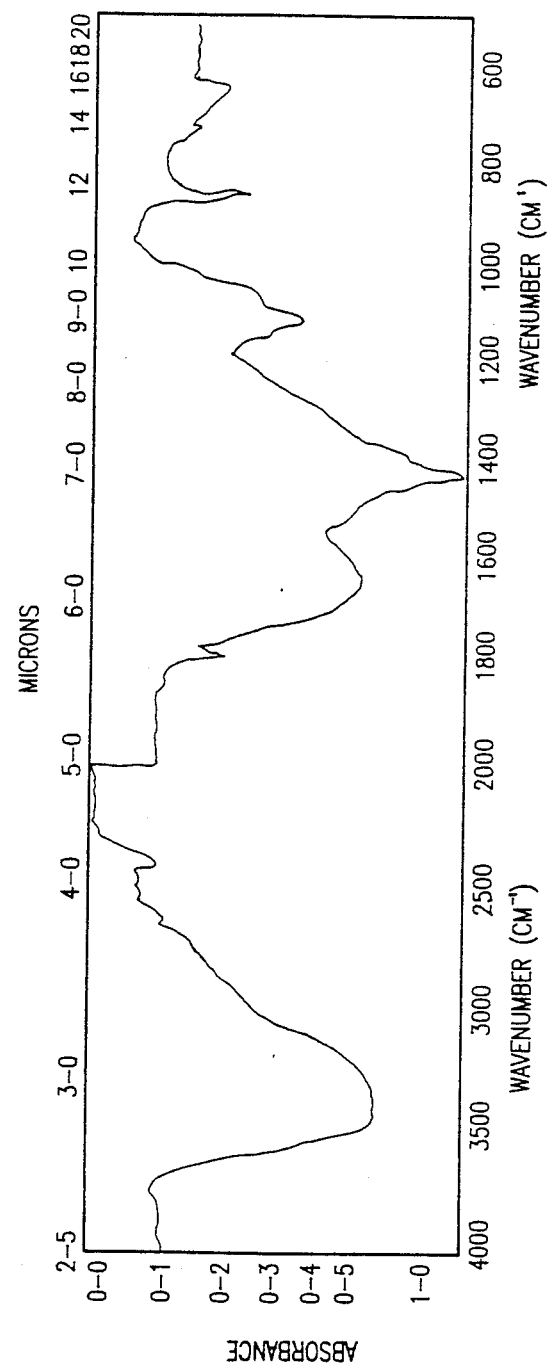
FIG. 5 shows an infrared curve of the antioxidant fraction C of the invention, isolated from spinach.

C: (see FIG. 5) broad bands at 3400 and 1600 cm.$^{-1}$, strong band at 1390 cm.$^{-1}$, additional bands at 1070 and 820 cm.$^{-1}$.

Figure 6:
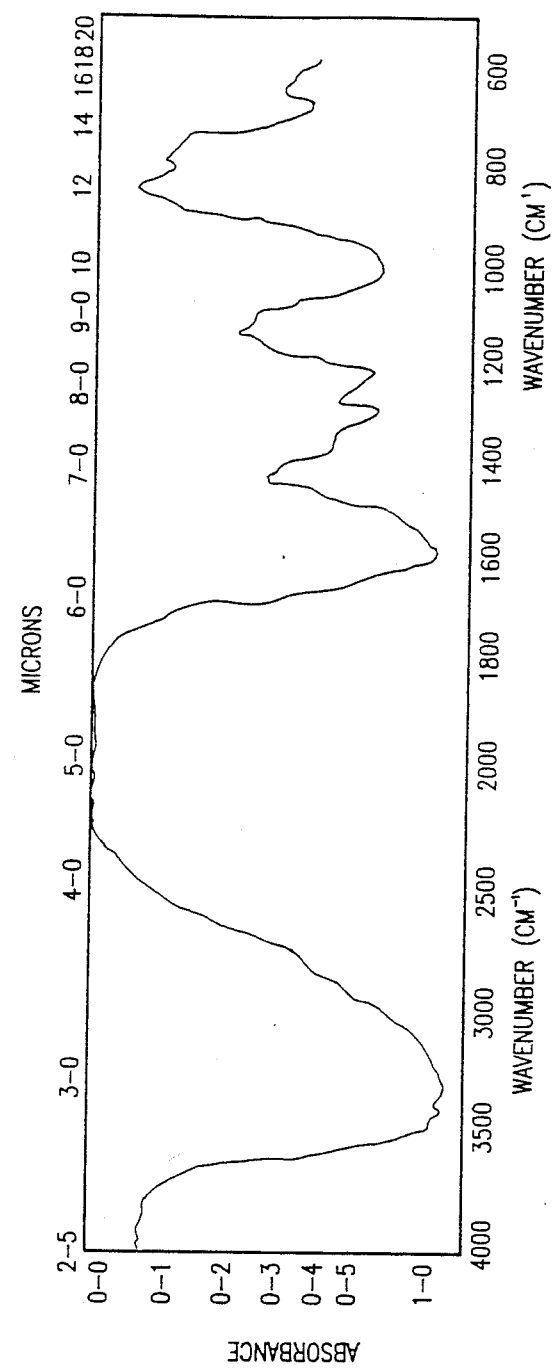
FIG. 6 shows an infrared curve of the antioxidant fraction $C_1$ of the invention, isolated from spinach.

$C_1$: (see FIG. 6) broad band at 3300 cm.$^{-1}$, strong band at 1620 cm.$^{-1}$, additional bands at 1390, 1320, 1080 and 770 cm.$^{-1}$.

$A_1$: (see FIG. 7) broad band at 3300-3400 cm.$^{-1}$, strong band at 1650 cm.$^{-1}$, addl. bands at 1730, 1540, 1250 and 1080 cm.$^{-1}$, weak bands at 2920, 1400 and 1150 cm.$^{-1}$.

EXAMPLE 2

Reduction of Peroxide Level in the Skin

Samples of lotions and appropriate controls were applied to mice or rat skin for a fixed period. The application was done once a day. Experiments were terminated by killing the animal, peeling the skin and freezing it in liquid nitrogen. Samples of the frozen skin were homogenized in 0.2M phosphate buffer, pH 6.5. After centrifugation, the supernatant was collected and analyzed for the peroxide value using the TBA (thiobarbituric acid) test as described by Sinnhuber et al, Food Res. 23: 620 (1958). In the experiments which follow, newborn (hairless) rats were used. It is generally considered that the penetration through the skin of newborn rats is better than in adult rats, since at this stage they have not yet developed any fur.

Test No. 1

In this experiment the control group was treated with petroleum jelly (known by the trade mark Vaseline) only, while the test group was treated with Vaseline containing a $C_1$ fraction. The test was run for 12 days and the results are presented in Table 1.

TABLE 1

| GROUP | TBA (O.D. 532/1 g. tissue) | Level of Peroxidation | P value* (n = 3) |
|---|---|---|---|
| Control | 0.295 | 100% | 0.002 |
| +0.5% $C_1$ | 0.188 | 64% | 0.002 |

*standard deviation

It is clearly demonstrated that the $C_1$ penetrates the skin of newborn rats and consequently reduces the level of peroxides in the skin. Since peroxides, and the free radicals involved in their formation and breakdown, constitute one of the main routes leading towards aging, the activity of this unique antioxidant can be considered as an anti-aging factor.

Test No. 2

In this experiment the antioxidant was dissolved in Oil of Olay (a proprietary skin lotion) obtained in Israel, in which the antioxidant has excellent solubility, and experiments similar to that described in No. 1 were performed. The results are presented in Table 2.

TABLE 2

| GROUP | TBA (O.D. 532/1 g. tissue) | Level of Peroxidation | P value* (n = 4) |
|---|---|---|---|
| Control (no treatment) | 0.295 | 100% | 0.002 |
| Control (Oil of Olay) | 0.230 | 78% | 0.005 |
| +0.15% $C_1$ | 0.200 | 68% | 0.011 |
| +1.5% $C_1$ | 0.191 | 65% | 0.010 |

*standard deviation

As in test No. 1, the antioxidant significantly reduced the level of peroxides in the skin. It is interesting to point out that in newborn rats, Oil of Olay without the antioxidant also reduced the peroxide level. This may be attributed to the commercial antioxidants present in the Oil of Olay which was used. It is possible that in newborn skin, due to its relatively high permeability, small amounts of these antioxidants can also penetrate the skin. However, in adult mice or rats, as will be shown later, Oil of Olay did not reduce the level of peroxides in the skin. On the contrary, in general, a small increase in peroxide level was detected, which perhaps may be attributed to traces of metals in the lotion.

EXAMPLE 3

Reduction of Peroxide Level in the Skin

In these experiments adult mice (2 months old) were treated as described in Example 2. The grown mice were shaved before applying the lotions to the skin.

In this experiment the antioxidant was dissolved in Oil of Olay. Mice were sacrificed after 21 days. The results are presented in Table 3.

TABLE 3

| GROUP | TBA (O.D. 532/1 g. tissue) | Level of Peroxidation | P value* (n = 3) |
|---|---|---|---|
| Control (no treatment) | 0.338 | 100% | 0.019 |
| Control (Oil of Olay) | 0.400 | 118% | 0.026 |
| +0.3% $C_1$ | 0.240 | 71% | 0.002 |

*standard deviation

It seems that in grown mice the Oil of Olay slightly increased the level of peroxides while addition of the antioxidant at a concentration of 0.3% significantly reduced these peroxides, thus indicating that even with grown mice the antioxidant penetrates the skin.

In similar experiments using 0.1% BHT, BHA and alpha tocopherol dissolved in Oil of Olay, no reduction of the level of peroxides was observed.

EXAMPLE 4

Reduction of Peroxide Level in the Skin

A new model for studying aging was developed. The new model involves the exposure of adult shaved mice to a UV lamp (sun lamp 300 W) for a short period. As a result, the aging processes as expressed by the level of peroxidation are stimulated and the effect of the present antioxidant was studied. Using this new technique, the optimal antioxidant dose for the inhibition of aging was determined.

In this experiment, a crude preparation of antioxidant (and not a purified antioxidant fraction) was used.

Adult mice were shaved and the individuals were exposed to the UV light (Philips HP 3115), with or without antioxidant, for a short period of one minute for two days (two exposures in total). On the third day they were sacrificed and the level of peroxidation in the skin was determined by the TBA (thiobarbituric acid) test.

Controls without exposure to the UV light were also included. Antioxidant was dissolved in Oil of Olay. The results are presented in Table 4.

TABLE 4

Effect of antioxidant dose on aging (7 individuals in each group)

| GROUP | TBA (O.D. 532/1 g. tissue) | Level of Peroxidation | P value* (n = 7) |
|---|---|---|---|
| 1. no radiation | 0.147 | 16.7% | 0.010 |
| 2. radiation + Oil of Olay | 0.880 | 100% | 0.027 |
| 3. radiation + 0.3% antioxidant in Oil of Olay | 0.740 | 84% | 0.006 |
| 4. radiation + 0.4% antioxidant in Oil of Olay | 0.680 | 77% | 0.020 |
| 5. radiation + 0.5% antioxidant in Oil of Olay | 0.680 | 77% | 0.011 |
| 6. radiation + 1.0% antioxidant in Oil of Olay | 0.700 | 79% | 0.006 |

*standard deviation

The optimal dose of crude antioxidant to be used is 0.3 to 0.4%.

EXAMPLE 5

Protection of the Skin Against the Effects of UV Radiation

Samples of human skin were obtained from a Plastic Surgery Department of a hospital. These samples were placed in a saline solution immediately after their removal from the patients. The skin samples were exposed to UV rays (Philips Sun Lamps) for 5 minute intervals, three successive times with a 5 minute rest period between each exposure. The distance between the lamp and the tissue was 12 cm. The skin samples were stored for 3 days at 4° C., after which time they were peeled and homogenized. 20-30 mg. of peeled tissue were assayed for peroxide level using the spectrophotometric TBA test.

The results clearly demonstrate that the peroxide level (aging) of the skin tissue was raised due to the exposure to UV rays. Skin treated with the present antioxidant and exposed to UV rays for the same period of time showed a peroxide level similar to the untreated control. These results are shown in Table 5.

TABLE 5

| Sample | TBA (O.D. 532/0.1 g. tissue) | Level of Peroxidation |
|---|---|---|
| Unexposed | 0.050 | 62.5% |
| Exposed | 0.080 | 100% |
| Exposed + Oil of Olay | 0.100 | 125% |
| Exposed + (A + B + C) + Oil of Olay | 0.050 | 62.5% |

The experiments run on human skin indicate the following:
(a) the antioxidant penetrates the skin;
(b) the antioxidant significantly reduces the level of peroxides;

(c) the antioxidant protects the skin against the aging effect of ultraviolet radiation.

It is also to be noted that when a mixture of fractions A+B+C was used, an effective antioxidant result was observed.

EXAMPLE 6

Toleration of the Antioxidants in Experimental Animals

The crude extract was tested in vivo for its effect on the immune response system in experimental mice. In these experiments, male Balb-C mice were injected intraperitoneally with 1 mg. of the crude extract from *Spinacia oleracea* per 0.2 ml. of phosphate buffer solution (PBS) per animal. Animals were sacrificed one, three and seven days after injection, following which their spleens were removed. Spleen cells ($10^7$ cells/ml. enriched RPMI) were cultured for 24 hours in the presence of CON A (concavalin-A) 2 μg./ml. and the supernatants thus obtained were tested for both IL-2 (interleukin-2) and CSF (colony stimulating factor). No significant differences were found between controls (i.e. animals receiving no treatment) and experimental animals, in their ability to produce IL-2 as well as CSF, indicating that the antioxidant has no adverse effect on the immune system. In addition, no pathological findings were observed in injected animals.

Additional testing determined that a single dose of 25 mg./mouse i.p. may be tolerated and that the $LD_{50}$ is in the range of 1400 mg./kg. for mice.

EXAMPLE 7

Anticancer Activity, and Toleration of the Antioxidants in Experimental Animals

The $C_1$ fraction was dissolved in PBS (50 mg./10 ml.) and 0.2 ml. of this solution was injected i.p. into each mouse twice weekly. The $C_1$ fraction was also administered orally in an aqueous solution (1 mg./ml.) and the mice were allowed to drink the solution from a calibrated bottle to enable measurement of the quantity of the $C_1$ fraction consumed by each individual mouse to be determined. Each mouse was subsequently injected with 0.6 mg. methylcholanthrene, a known inducer of fibrosarcoma. Test series A and B were carried out as follows, in which the figures refer to number of animals in which the appearance of tumors occurred/ the number of animals in the group:

| Weeks after inoculation with methylcholanthrene | Controls | Groups treated with C1 antioxidant | |
|---|---|---|---|
| | | orally | i.p. |
| (TEST A) | | | |
| 5 | 4/20 | 1/10 | 1/10 |
| 6 | 9/20 | 1/10 | 1/10 |
| 7 | 14/20 | 3/10 | 2/10 |
| 8 | 16/20 | 3/10 | 2/10 |
| 9 | 18/20 | 4/10 | 2/10 |
| (TEST B) | | | |
| 7 | 1/10 | 0/8 | 0/9 |
| 8 | 3/10 | 0/8 | 0/9 |
| 9 | 4/10 | 0/8 | 0/9 |
| 10 | 4/10 | 0/8 | 0/9 |
| 11 | 6/10 | 1/8 | 0/9 |
| 12 | 7/10 | 1/8 | 0/9 |
| 13 | 7/10 | 2/8 | 1/9 |

At week 13 (test B), after as many as 25–29 injections, one mouse from each group was sacrificed and observed for gross internal changes (i.e. lymph nodes, spleen, liver, kidney, heart and lung, etc.); no significant changes and no pathological damage were observed. This demonstrated that even a prolonged treatment with the $C_1$ fraction by different routes of administration did not cause any damage to the treated mice.

The in vivo experiments demonstrated that i.p. or oral administration with $C_1$ is effective in delaying the appearance and reducing the frequency of methylcholanthrene-induced tumors.

EXAMPLE 8

Effect of the Antioxidants on Skin Texture

Skin tests on human volunteers using a 0.3% w/w dispersion of the crude antioxidant extract in Oil of Olay have resulted in subjective improvement in the texture of the skin with no adverse effects in any test subjects.

EXAMPLE 9

This example is illustrative of topically administered compositions which may be used in the practice of the invention.

| Lotion | |
|---|---|
| Antioxidant | 1.0 g. |
| Base* | 99.0 g. |
| | 100.0 g. |
| *stearic acid | 1.4 g. |
| triethanolamine | 0.6 g. |
| glyceryl monostearate | 4.0 g. |
| lanolin, hydrous | 1.0 g. |
| cetyl alcohol | 0.4 g. |
| mineral oil | 2.0 g. |
| methyl parahydroxybenzoate | 0.1 g. |
| distilled water | 90.5 g. |
| (+ perfume) | 100.0 g. |
| Cream | |
| antioxidant | 1.0 g. |
| cetyl alcohol | 6.4 g. |
| stearyl alcohol | 7.4 g. |
| isopropyl myristate | 2.0 g. |
| sodium lauryl sulfate | 1.4 g. |
| white petrolatum | 27.6 g. |
| propylene glycol | 9.2 g. |
| water, to make | 100.0 g. |

EXAMPLE 10

Antioxidant Activity of the Plant-extracted Materials

Figure 2:
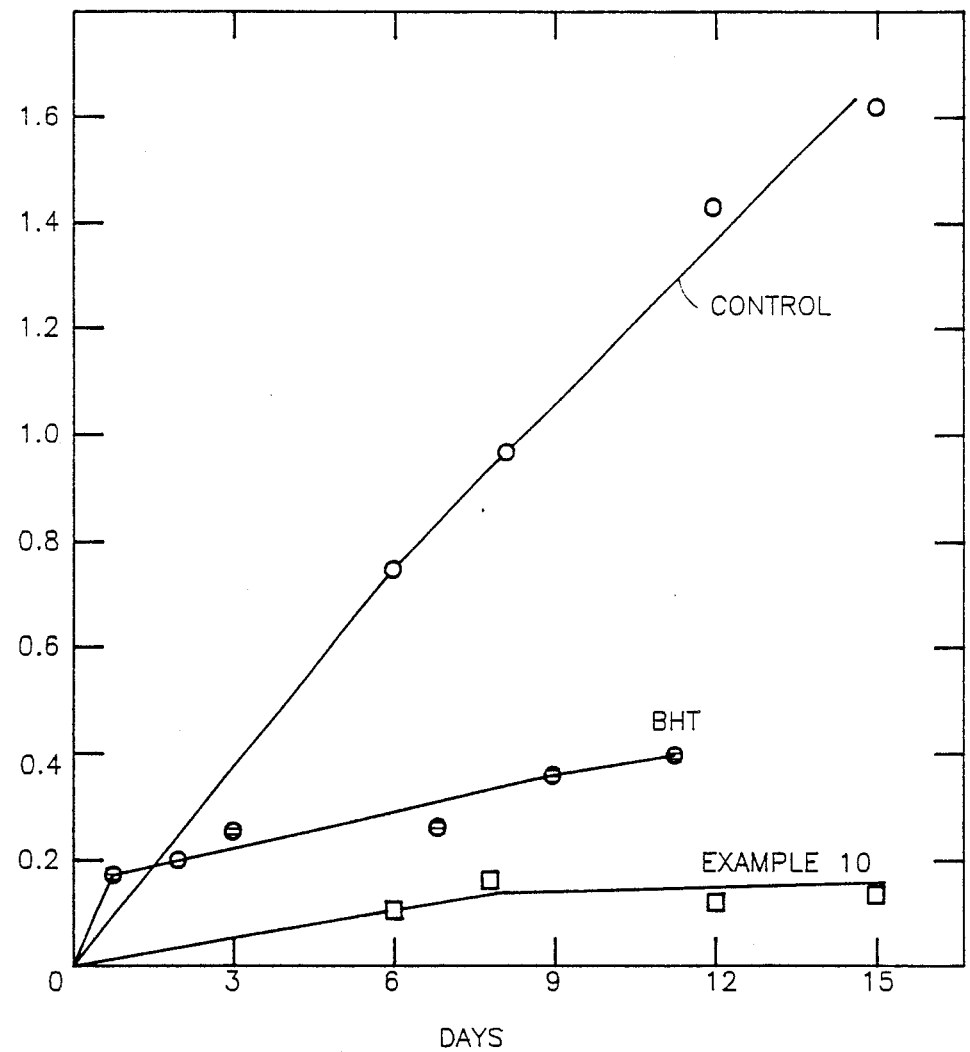
FIG. 2 shows a graphical comparison of the antioxidant effect of the composition of the invention with BHT.

The crude antioxidant (containing A, B and C) was added to linoleic acid to form a mixture containing 20 ml. of $7.5 \times 10^{-3}$M linoleic acid in 0.2M aqueous sodium phosphate buffer (pH 6.5), containing 0.25% Tween 20 (R) and 1 mg. of the crude antioxidant. Controls were run which contained the buffer and Tween 20 but no antioxidant, as well as a sample of linoleic acid with 1 mg. of BHT and the same dispersant system. The mixture was kept at 30° C. and the optical density was determined using the ferric thiocyanate method described by R. B. Koch et al in Arch. Biochem. Biophys. 78: 165 (1959). The test results depicted in FIG. 2 show that the antioxidant of the invention is more effective than BHT in preventing oxidation of linoleic acid.

EXAMPLE 11

Isolation of Antioxidant Materials from Clover

A similar procedure to that described for spinach, was applied to isolate antioxidant materials from clover (*trifolium alexandrinum*). The crude extract was separated on Sephadex G-25 to give fractions A, B and C. Fraction A was purified on Ecteola to give fraction $A_1$. Fraction C was resolved on Sephadex G-10 to give fractions $C_1$ and $C_2$. Fraction $C_1$ was further resolved by dissolving in a minimum amount of water, applying to 0.2 mm. silica gel plates and developing in 30:60 v/v $H_2O$-ethanol, to give fractions labelled TLC-1, -2 and -3.

Figure 8:
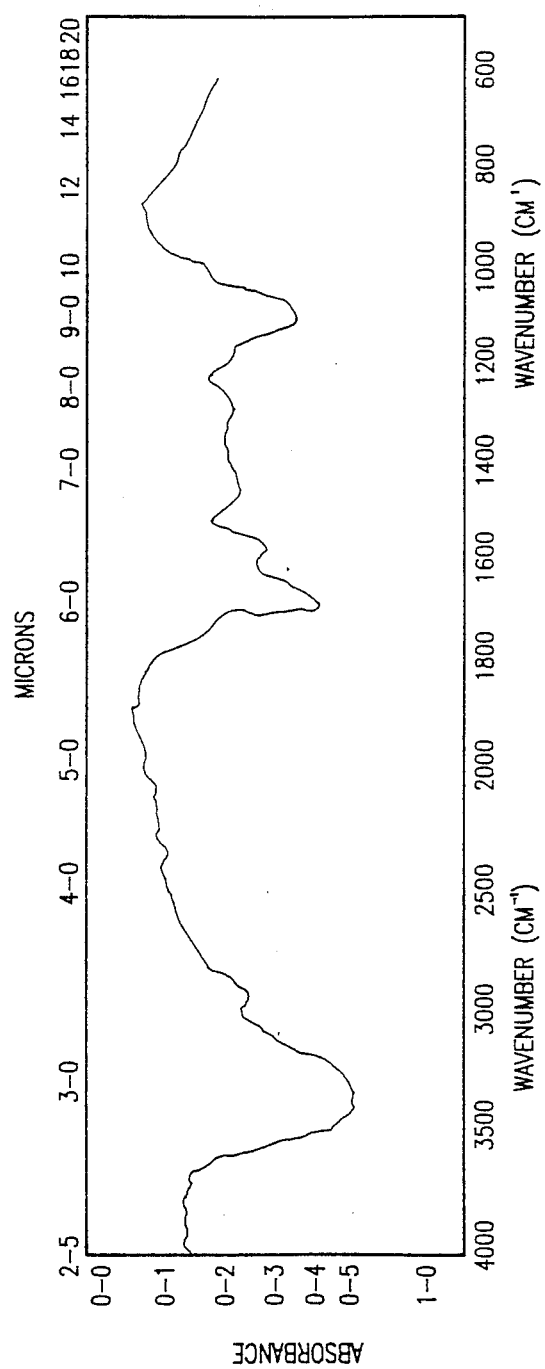
FIG. 8 shows an infrared curve of the antioxidant fraction A of the invention, isolated from clover.

The following infrared data was obtained:

A: (see FIG. 8) similar to the analogous spinach fraction.

Figure 9:
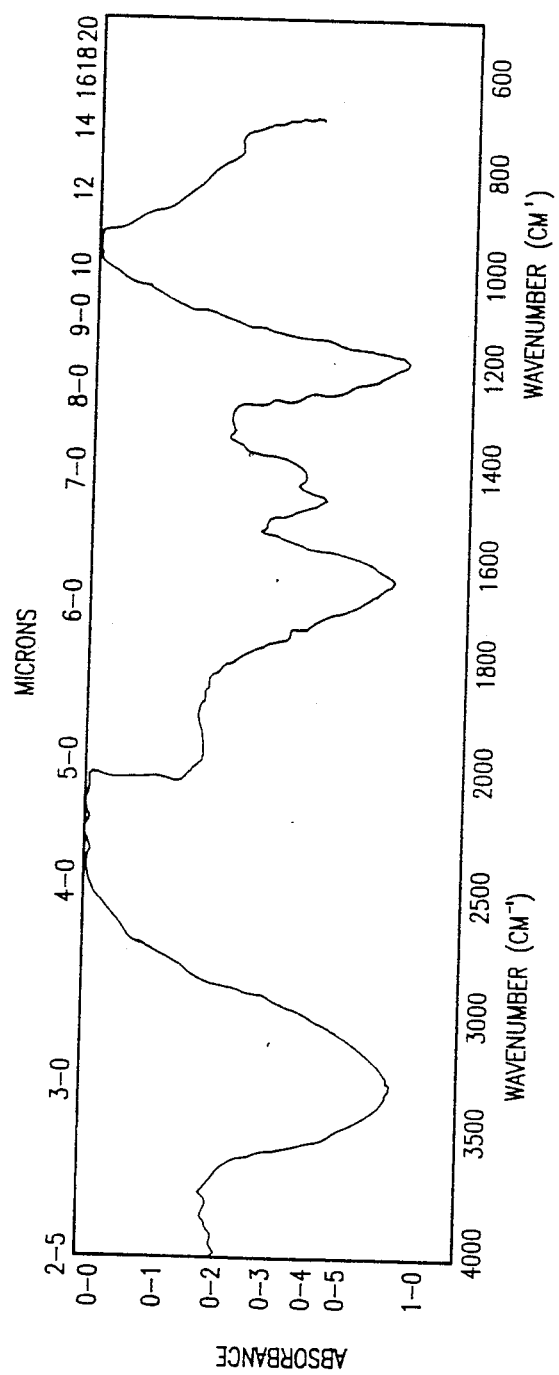
FIG. 9 shows an infrared curve of the antioxidant fraction B of the invention, isolated from clover.

B: (see FIG. 9) strong and broad bands at 3300, 1560 and 1130 cm.$^{-1}$, medium band at 1400 cm.$^{-1}$, weak bands at 1350 and 1430 cm.$^{-1}$.

Figure 10:
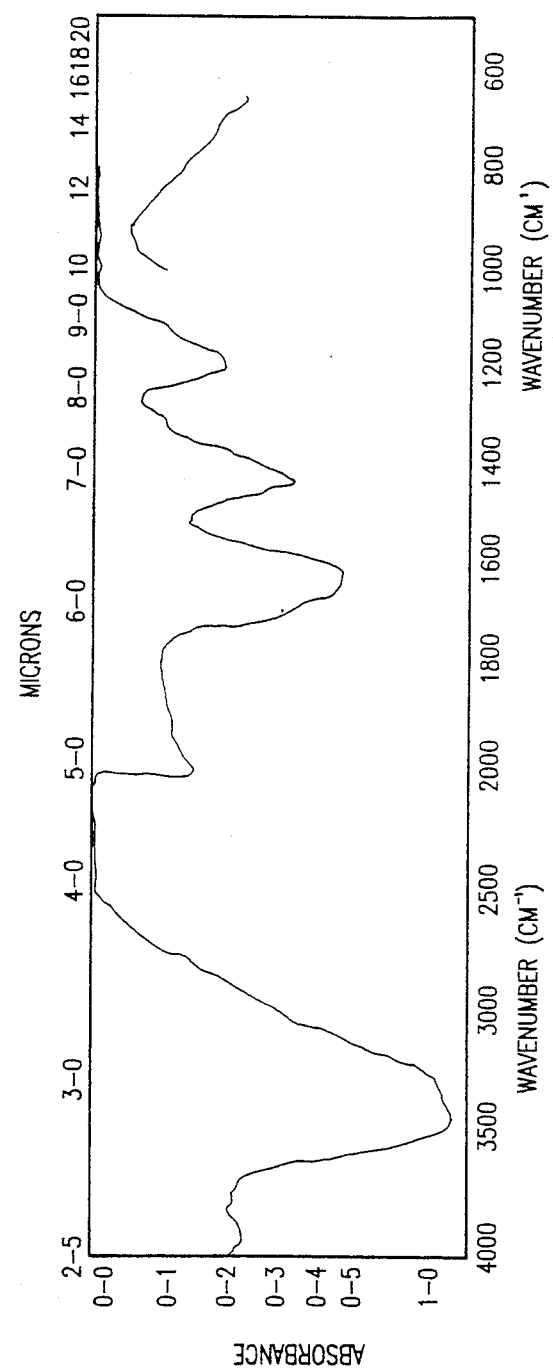
FIG. 10 shows an infrared curve of the antioxidant fraction C of the invention, isolated from clover.

C: (see FIG. 10) broad band at 3430 cm.$^{-1}$, strong bands at 1600, 1380 and 1150 cm.$^{-1}$.

Figure 11:
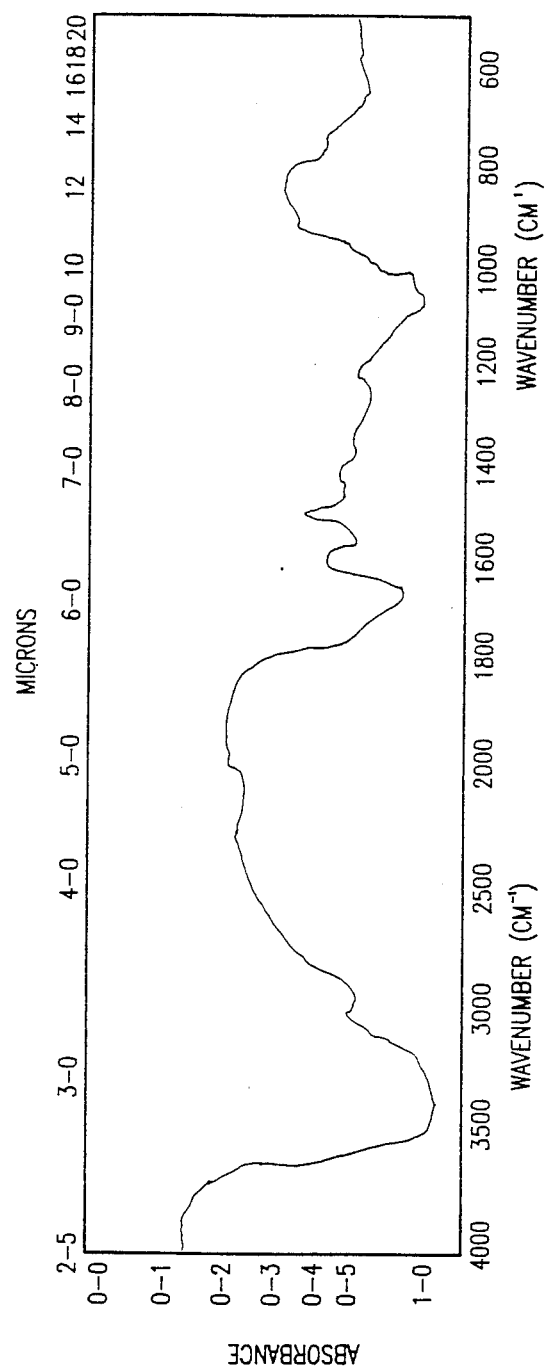
FIG. 11 shows an infrared curve of the antioxidant fraction $A_1$ of the invention, isolated from clover.

$A_1$: (see FIG. 11) similar to the analogous spinach fraction.

Certain of the foregoing fractions (0.2 mg. in each case) derived from clover were tested as antioxidant in a system which contained linoleic acid as substrate and the enzyme lipoxygenase as catalyst. Oxygen absorption was followed using an oxygen monitor according to Grossman and Zakut, in Methods of Biochemical Analysis (D. Glick, Ed.) 25: 303–29 (1979). The following results were obtained.

| Inhibition of Lipid Peroxidation by Antioxidants from Clover. | |
|---|---|
| Fraction | % Inhibition |
| crude extract | 20 |
| A | 9 |
| B | 16 |
| C | 30 |
| TLC-1 | 42 |
| TLC-3 | 46 |

EXAMPLE 12

Isolation of Antioxidant Materials from Algae

A number of algae samples were homogenized with distilled water and an extract was prepared according to the technique described above for spinacia oleracea. The crude homogenate was centrifuged, and the supernatant was collected and dried by lyophilization. The dried crude extracts were tested as antioxidants in a system which contained linoleic acid as a substrate and the enzyme lipoxygenase as catalyst. Oxygen absorption was followed using an oxygen monitor according to Grossman and Zakut, in Methods of Biochemical Analysis (D. Glick, Ed.) 25: 303–29 (1979). The following results were obtained using 2.5 mg. crude extract.

| Inhibition of Lipid Peroxidation by Antioxidants from Algae. | |
|---|---|
| Algae | % Inhibition |
| Spirulina | 30 |
| Nicractinium | 27 |
| Synichococcus | 30 |
| Navicola | 42 |
| Euglena | 35 |
| Red | 35 |

EXAMPLE 13

Treatment of Warts with the Present Antioxidants

In all of these tests, there was used an approximately 1% solution of the isolated crude antioxidant (which had not been subjected to chromatographic separation), dissolved in water.

(a) About 21 months prior to commencing the present treatment, a patient had warts on the hands removed surgically, but they reappeared about three weeks thereafter. Approximately one year following surgery, a proprietary solution which contained copper ions 15 ppm, oxalic acid 40 mg./l., lactic acid 3 mg./l., acetic acid 40 mg./l. and nitrate 410 mg./l., was applied topically to the patient's warts, 2-3 times daily for two weeks; in the course of this treatment, the warts became discolored and appeared to be diminished, but several days after discontinuing the treatment, the warts resumed their previous appearance. The present treatment consisted of bathing the hands in the above-mentioned aqueous antioxidant solution, at random intervals over a period of 3 days. At the end of that time all of the 30 warts present on the hands had disappeared, and had not reappeared by the end of a 6-month observation period.

(b) 6 months prior to commencing the present treatment, a patient having two large warts on the fingers had them surgically removed, but they reappeared a few weeks thereafter. The present treatment consisted of bathing the affected fingers in the above-mentioned aqueous solution, once or twice daily (for 5-10 minutes each time) for two weeks. At the end of that time the warts had disappeared, and had not reappeared by the end of a 6-month observation period.

(c) The above-mentioned aqueous antioxidant solution was applied with a pad to the warts on the hands of 2 patients, 1-2 times daily over a period of three weeks. At the end of that time the warts had disappeared, and had not reappeared by the end of a 6-month observation period.

While the invention has been described above with respect to its presently preferred embodiments, it will be apparent to those skilled in the art that many variations and modifications may be made. The invention is accordingly not to be construed as restricted to the illustrated embodiments, rather its scope will be defined in the claims which follow.

We claim:

1. A method for treating warts, which comprises applying to skin having warts thereon, a water soluble antioxidant material of plant origin which is characterized by stability for an extended period of time under ambient temperature and pressure, at least in the dry state, and by the fact that it provides an antioxidant effect when applied to the skin, said material of plant origin having been obtained by a step of water extraction of tissue selected from stem and leaf tissue from plants selected from the group consisting of Trifolium, Medicago, Nicotiana, Zea, Pennisetum, Algae and Allium, and members of the order Chenopodiales.

2. A method according to claim 1, wherein said plants are selected from the group consisting of members of the families Chenopodiaceae and Aizoaceae.

3. A method according to claim 2, wherein said plants are selected from the group consisting of Spinacia, Atriplex, Beta and Tetragonia.

4. A method according to claim 1, wherein the said stem and leaf tissue is constituted by fresh stem and leaf tissue.

5. A method according to claim 1, wherein said material of plant origin is chromatographically separable on dextran which has been cross-linked with epichlorohydrin and has a pore size of 50-150 μm, into antioxidant fractions which are colored brown(A), yellow(B) and orange(C), and of which fraction A is chromatographically purifiable on a substrate selected from the group consisting of (i) a condensation product of cellulose with epichlorohydrin and triethanolamine having a capacity of 0.3 to 0.4 meq./g. and a particle size 0.05-0.2 mm., and (ii) dextran which has been cross-linked with epichlorohydrin and has a pore size of 40-120 μm, to give an antioxidant fraction ($A_1$) having an infrared spectrum with substantially the following features, namely, broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$, and of which fractions, fraction C is chromatographically separable on dextran which has been cross-linked with epichlorohydrin and has a pore size of 40-120 μm, into antioxidant fractions colored dark brown($C_1$) and yellow orange($C_2$).

6. A method according to claim 5, wherein said material comprises at least one substance selected from fractions A, $A_1$, B, $C_1$ and $C_2$.

7. A method according to claim 6, wherein said material comprises a combination of at least two substances selected from the group consisting of fractions A, $A_1$, B, $C_1$ and $C_2$.

8. A method according to claim 1, wherein said material is selected from the group consisting of chromatographic fractions identified by the labels (a), (b), (c), (d), (e), (f) and (g), said fractions being respectively characterized by an infrared spectrum with substantially the following features:
   (a) broad band at 3400 cm.$^{-1}$, strong bands at 1050 and 1650 cm.$^{-1}$, weak bands at 1250 and 1430 cm.$^{-1}$;
   (b) broad bands at 3400, 1640 and 1080 cm.$^{-1}$, additional bands at 1420, 1300 and 810 cm.$^{-1}$;
   (c) broad bands at 3400 and 1600 cm.$^{-1}$, strong band at 1390 cm.$^{-1}$, additional bands at 1070 and 820 cm.$^{-1}$;
   (d) broad band at 3300 cm.$^{-1}$, strong band at 1620 cm.$^{-1}$, additional bands at 1390, 1320, 1080 and 770 cm.$^{-1}$;
   (e) broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;
   (f) strong and broad bands at 3300, 1560 and 1130 cm.$^{-1}$, medium band at 1400 cm.$^{-1}$, weak bands at 1350 and 1430 cm.$^{-1}$;
   (g) broad band at 3430 cm.$^{-1}$, strong bands at 1600, 1380 and 1150 cm.$^{-1}$.

9. A method according claim 1, wherein said material of plant origin is subjected to a subsequent step of chromatographic fractionation.

10. A method according to claim 9, wherein said fractionation comprises chromatographically separating said extract on dextran which has been cross-linked with epichlorohydrin and has a pore size of 50-150 μm, into fractions which are colored brown(A), yellow(B) and orange(C).

11. A method according to claim 10, wherein said fractions are subjected to at least one of the following chromatographic purification procedures, namely:
   chromatographically purifying fraction A on a substrate selected from the group consisting of (i) a condensation product of cellulose with epichlorohydrin and triethanolamine having a capacity of 0.3 to 0.4 meq./g. and a particle size 0.05-0.2 mm., and
   (ii) dextran which has been cross-linked with epichlorohydrin and has a pore size of 4-120 μm, to give a fraction($A_1$) having an infrared spectrum with substantially the following features, namely, broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;
   chromatographically separating fraction C on dextran which has been cross-linked with epichlorohydrin and has a pore size of 40-120 μm, into fractions colored dark brown($C_1$) and yellow orange($C_2$).

12. A method according to claim 1, wherein said material is applied in the form of a composition which comprises also an inert diluent or carrier which is adapted for application to the skin.

13. A method according to claim 12, wherein said composition contains from about 0.005 to about 5% by weight of said antioxidant material, based upon the total weight of the composition.

14. A method according to claim 12, wherein said composition is in a form selected from the group consisting of a gel, ointment, salve, hydrophilic cream, hydrophilic lotion, hydrophobic cream, hydrophobic lotion, and an aqueous solution.

15. A method according to claim 12, wherein said composition comprises additionally a local anaesthetic.

16. A method for treating warts, which comprises the steps of:
   comminuting plant tissue selected from fresh leaf and stem tissue of plants selected from the group consisting of Trifolium, Medicago, Nicotiana, Zea, Pennisetum, Algae and Allium, and members of the order Chenopodiales;
   extracting thus comminuted tissue with water at a temperature between about 4° C. and the boiling point of the mixture of water and comminuted tissue, to obtain a crude aqueous extract;
   subjecting the crude aqueous extract to chromatographic separation;
   testing for antioxidant activity a material selected from the group consisting of the crude aqueous extract and the fractions obtained by said chromatographic separation step;
   selecting a material from the tested group which gives a positive result in said testing step; and
   applying to skin having warts thereon, at least one material which is thus selected.

17. A method according to claim 16, wherein said testing step is followed by an additional step of verifying that said material is characterized by stability in the dry state for an extended period of time under ambient temperature and pressure, and said selecting step comprises selecting a material from the said tested group which gives a positive result in both said testing and said verifying steps.

18. A method according to claim 16, wherein said plant tissue is obtained from plants which are selected from the group consisting of members of the families Chenopodiaceae and Aizoaceae.

19. A method according to claim 18, wherein said plant tissue is obtained from plants of the group consisting of Spinacia, Atriplex, Beta and Tetragonia.

20. A method according to claim 16, wherein said chromatographic separation step is effected on dextran which has been cross-linked with epichlorohydrin and has a pore size of 50-150 μm.

21. A method according to claim 20, wherein said chromatographic separation step further includes the sub-step of chromatographic purification of any obtained fraction on a substrate selected from the group consisting of (i) a condensation product of cellulose with epichlorohydrin and triethanolamine having a capacity of 0.3 to 0.4 meq./g. and a particle size 0.05–0.2 mm., and (ii) dextran which has been cross-linked with epichlorohydrin and has a pore size of 40–120 µm.

22. A method according to claim 16, wherein said at least one thus selected material comprises at least one material selected from the group consisting of chromatographic fractions identified by the labels (a), (b), (c), (d), (e), (f), (g) and (h), said fractions being respectively characterized by an infrared spectrum with substantially the following features:
- (a) broad band at 3400 cm.$^{-1}$, strong bands at 1050 and 1650 cm.$^{-1}$, weak bands at 1250 and 1430 cm.$^{-1}$;
- (b) broad bands at 3400, 1640 and 1080 cm.$^{-1}$, additional bands at 1420, 1300 and 810 cm.$^{-1}$;
- (c) broad bands at 3400 and 1600 cm.$^{-1}$, strong band at 1390 cm.$^{-1}$, additional bands at 1070 and 820 cm.$^{-1}$;
- (d) broad band at 3300 cm.$^{-1}$, strong band at 1620 cm.$^{-1}$, additional bands at 1390, 1320, 1080 and 770 cm.$^{-1}$;
- (e) broad band at 3300–3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;
- (f) strong and broad bands at 3300, 1560 and 1130 cm.$^{-1}$, medium band at 1400 cm.$^{-1}$, weak bands at 1350 and 1430 cm.$^{-1}$;
- (g) broad band at 3430 cm.$^{-1}$, strong bands at 1600, 1380 and 1150 cm.$^{-1}$;
- (h) broad band at 3300–3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$.

23. A method according to claim 16, wherein said at least one thus selected material comprises a mixture of at least two different thus selected materials.

24. A method according to claim 22, wherein said at least one thus selected material comprises a mixture of at least two different thus selected materials.

25. A method according to claim 16, wherein said at least one thus selected material is formulated as a composition which comprises also an inert diluent or carrier adapted for application to the skin, prior to applying to the skin.

26. A method according to claim 25, wherein said composition contains from about 0.005 to about 5% by weight of said antioxidant material, based upon the total weight of the composition.

27. A method according to claim 25, wherein said composition is in a form selected from the group consisting of a gel, ointment, salve, hydrophilic cream, hydrophilic lotion, hydrophobic cream, hydrophobic lotion, and an aqueous solution.

28. A method according to claim 25, wherein said composition comprises additionally a local anaesthetic.

29. A method for treating warts, which comprises the steps of:
- extracting with water plant tissue selected from leaf and stem tissue of plants selected from the group consisting of Trifolium, Medicago, Nicotiana, Zea, Pennisetum, Algae and Allium, and members of the order Chenopodiales, to obtain a crude aqueous extract having antioxidant activity;
- subjecting the crude aqueous extract to chromatographic separation, to obtain fractions having antioxidant activity; and
- applying to skin having warts thereon at least one material selected from the group consisting of said crude aqueous extract and said fractions.

30. A method according to claim 29, wherein said plant tissue is obtained from plants which are selected from the group consisting of members of the families Chenopodiaceae and Aizoaceae.

31. A method according to claim 30, wherein said plant tissue is obtained from plants of the group consisting of Spinacia, Atriplex, Beta and Tetragonia.

32. A method according to claim 29, wherein said at least one thus selected material comprises at least one material selected from the group consisting of chromatographic fractions identified by the labels (a), (b), (c), (d), (e), (f), (g) and (h), said fractions being respectively characterized by an infrared spectrum with substantially the following features:
- (a) broad band at 3400 cm.$^{-1}$, strong bands at 1050 and 1650 cm.$^{-1}$, weak bands at 1250 and 1430 cm.$^{-1}$;
- (b) broad bands at 3400, 1640 and 1080 cm.$^{-1}$, additional bands at 1420, 1300 and 810 cm.$^{-1}$;
- (c) broad bands at 3400 and 1600 cm.$^{-1}$, strong band at 1390 cm.$^{-1}$, additional bands at 1070 and 820 cm.$^{-1}$;
- (d) broad band at 3300 cm.$^{-1}$, strong band at 1620 cm.$^{-1}$, additional bands at 1390, 1320, 1080 and 770 cm.$^{-1}$;
- (e) broad band at 3300–3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;
- (f) strong and broad bands at 3300, 1560 and 1130 cm.$^{-1}$, medium band at 1400 cm.$^{-1}$, weak bands at 1350 and 1430 cm.$^{-1}$;
- (g) broad band at 3430 cm.$^{-1}$, strong bands at 1600, 1380 and 1150 cm.$^{-1}$;
- (h) broad band at 3300–3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$.

33. A method according to claim 29, wherein said at least one thus selected material comprises a mixture of at least two different thus selected materials.

34. A method according to claim 32, wherein said at least one thus selected material comprises a mixture of at least two different thus selected materials.

35. A method according to claim 29, wherein said at least one thus selected material is formulated as a composition which comprises also an inert diluent or carrier adapted for application to the skin, prior to applying to the skin.

36. A method according to claim 35, wherein said composition contains from about 0.005 to about 5% by weight of said antioxidant material, based upon the total weight of the composition.

37. A method according to claim 35, wherein said composition is in a form selected from the group consisting of a gel, ointment, salve, hydrophilic cream, hydrophilic lotion, hydrophobic cream, hydrophobic lotion, and an aqueous solution.

38. A method according to claim 35, wherein said composition comprises additionally a local anaesthetic.

* * * * *